United States Patent [19]

Brunelle et al.

[11] Patent Number: 4,638,077

[45] Date of Patent: Jan. 20, 1987

[54] METHOD FOR THE PREPARATION OF CHLOROFORMATE COMPOSITIONS

[75] Inventors: Daniel J. Brunelle, Scotia; Thomas G. Shannon, Schenectady, both of N.Y.; Niles R. Rosenquist, Evansville, Ind.

[73] Assignee: General Electric Company, Schenectady, N.Y.

[21] Appl. No.: 790,909

[22] Filed: Oct. 24, 1985

Related U.S. Application Data

[63] Continuation-in-part of Ser. No. 676,353, Nov. 29, 1984.

[51] Int. Cl.$^4$ .............................................. C01B 31/24
[52] U.S. Cl. .................................... 558/281; 558/280; 558/282
[58] Field of Search ................ 260/463; 558/280, 281, 558/282

[56] References Cited

U.S. PATENT DOCUMENTS

| | | | |
|---|---|---|---|
| 2,873,291 | 2/1959 | Spiegler | 260/463 |
| 3,189,640 | 6/1965 | Dietrich et al. | 260/463 |
| 3,211,775 | 10/1965 | Stephens et al. | 260/463 |
| 3,255,230 | 6/1966 | Kurkjy et al. | 260/463 |
| 3,312,661 | 4/1967 | Kurkjy et al. | |
| 3,312,662 | 4/1967 | Kurkjy et al. | 260/463 X |
| 3,334,128 | 8/1967 | Brown | 260/463 |
| 3,527,734 | 9/1970 | Matzner | 260/463 X |
| 3,910,983 | 10/1975 | Merkel et al. | 260/463 |
| 3,959,335 | 5/1976 | Vernaleken et al. | 260/463 |
| 3,966,785 | 6/1976 | Krimm et al. | 260/463 |
| 3,974,126 | 8/1976 | Narita et al. | 260/463 X |
| 4,025,489 | 5/1977 | Bailey et al. | 260/463 X |

*Primary Examiner*—Bernard Helfin
*Attorney, Agent, or Firm*—William H. Pittman; James C. Davis, Jr.; James Magee, Jr.

[57] ABSTRACT

Chloroformate compositions, particularly bischloroformate compositions, are prepared by the reaction of phosgene with a hydroxy compound, preferably a dihydroxy compound such as bisphenol A, in a heterogeneous mixture, while adding a hydrogen chloride scavenger comprising aqueous base as necessary and maintaining a pH of 0.5–8 during the phosgene addition. When a polyhydroxy compound is employed and the temperature is above 30° C., the phosgene addition rate is maintained at a level high enough to effect rapid and complete reaction with dissolved hydroxy compound. This method uses substantially less phosgene than methods involving a higher pH.

10 Claims, No Drawings

METHOD FOR THE PREPARATION OF CHLOROFORMATE COMPOSITIONS

This application is a continuation-in-part of copending application Ser. No. 676,353, filed Nov. 29, 1984 and now abandoned.

This invention relates to chloroformate compositions useful in the preparation of various polycarbonates and other materials. More particularly, it relates to novel bischloroformate compositions and a method for their preparation.

Chloroformates are a known class of useful organic intermediates. In particular, bischloroformates of dihydroxy compounds and their oligomers are known to be useful for the production of polycarbonates. They may also be used as intermediates in the preparation of cyclic polycarbonate oligomers which may be converted to very high molecular weight polycarbonates, as disclosed in copending, commonly owned application Ser. No. 704,122, filed Feb. 22, 1985, the disclosure of which is incorporated by reference herein.

A number of methods of making chloroformates are known in the art. For example, U.S. Pat. No. 3,189,640 describes the preparation of bischloroformate compositions by reacting a water-soluble salt of an alkylidene diphenol with phosgene in a buffered aqueous system. Similar methods of making mono- and bischloroformates, sometimes employing an organic diluent as well as the aqueous medium, are disclosed in U.S. Pat. Nos. 3,312,661, 3,959,335, 3,974,126 and 3,966,785. All of these methods require that the pH of the reaction mixture be maintained on the alkaline side, typically in the 9–12 range and in certain instances above 12. In another method described in U.S. Pat. No. 3,255,230, a dihydric phenol is reacted with phosgene in an inert organic solvent medium in the presence of a quaternary ammonium catalyst.

The methods described in the above-noted prior art suffer from a number of disadvantages. In the first place, the bischloroformate products thus obtained frequently contain substantial amounts of oligomer bischloroformates containing as many as 15 repeating units derived from the dihydroxy compound. In the second place, they often require a substantial excess of phosgene over the stoichiometric amount, the mole ratio of phosgene to dihydroxy compound in some cases being as high as 5:1 (i.e., a ratio of equivalents as high as 2.5:1 as defined hereinafter). While phosgene is not a particularly expensive chemical reagent, it is highly toxic and care must therefore be taken to avoid its discharge into the atmosphere. Unreacted phosgene is normally destroyed by quenching with sodium hydroxide and neutralizing the sodium carbonate solution thus formed with mineral acid, thus generating a large amount of carbon dioxide. Such protective methods are cumbersome.

A principal object of the present invention, therefore, is to provide novel chloroformates, especially dihydroxy compound bischloroformate compositions, and a method for their preparation.

A further object is to provide a chloroformate preparation method which requires a minimum amount of phosgene.

A further object is to prepare bischloroformate compositions which are useful for the preparation of cyclic polycarbonate oligomer mixtures.

A still further object is to provide compositions containing principally monomeric, dimeric and trimeric dihydroxy compound bischloroformates, as well as a method for their preparation.

Other objects will in part be obvious and will in part appear hereinafter.

In one of its aspects, the present invention is directed to bischloroformate compositions consisting essentially of compounds having the formula

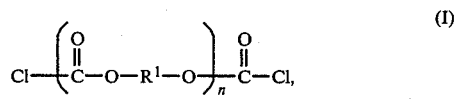

wherein $R^1$ is a divalent aliphatic, alicyclic or aromatic radical and n is at least 1; about 45–90% by weight of the chloroformate constituents of said compositions being the compound wherein n is 1 and no more than 10% thereof being compounds wherein n is greater than 3.

The $R^1$ values which are aliphatic or alicyclic in the compositions of this invention generally contain up to about 8 carbon atoms. Illustrative $R^1$ values are ethylene, propylene, trimethylene, tetramethylene, hexamethylene, dodecamethylene, poly-1,4-(2-butenylene), poly-1,10(2-ethyldecylene), 1,3-cyclopentylene, 1,3-cyclohexylene, 1,4-cyclohexylene, m-phenylene, p-phenylene, naphthylene, 4,4'-diphenylene, 2,2-bis(4-hydroxyphenylene)propylidene, benzene-1,4-dimethylene (which is a vinylog of the ethylene radical and has similar properties) and substituted derivatives thereof. Illustrative substituents (one or more) are alkyl, cycloalkyl, alkenyl (e.g., crosslinkable-graftable moieties such as vinyl and allyl), halo (especially fluoro, chloro and/or bromo), nitro and alkoxy.

The $R^1$ values are usually aromatic and preferably have the formula

wherein each of $A^1$ and $A^2$ is a single-ring divalent aromatic radical and Y is a bridging radical in which one or two atoms separate $A^1$ from $A^2$. The free valence bonds in formula II are usually in the meta or para positions of $A^1$ and $A^2$ in relation to Y.

In formula II, the $A^1$ and $A^2$ values may be unsubstituted phenylene or substituted derivatives thereof wherein the substituents are as defined for $R^1$. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated $C_{1-12}$ aliphatic or alicyclic radical such as methylene, cyclohexylmethylene, 2-[2.2.1]bicycloheptylmethylene, ethylene, ethylidene, isopropylidene, neopentylidene, cyclohexylidene, cyclopentadecylidene, cyclododecylidene or adamantylidene, especially an alkylidene radical. Aryl-substituted radicals are included, as are unsaturated radicals and radicals containing atoms other than carbon and hydrogen; e.g., oxy groups. Substituents such as those previously enumerated may be present on the aliphatic, alicyclic and aromatic portions of the Y group. For reasons of availability and particular suitability for the purposes of this invention, the preferred radical of formula II is the 2,2-bis(4-phenylene)propane radical, which is derived from bisphenol A and in which Y is 2,2-propylidene and $A^1$ and $A^2$ are each p-phenylene.

The distributions of the molecular species in the bischloroformate compositions have been determined by reversed phase high pressure liquid-liquid chromatography. The composition was first reacted with an equimolar mixture of phenol and triethylamine to produce the corresponding phenyl esters, which are resistant to hydrolysis under chromatography conditions. The phenyl esters were dissolved in a mixture of tetrahydrofuran and water and chromatographed using a relatively non-polar packing, whereupon lower molecular weight constituents were eluted first. For each molecular species, two values were determined and used for identification: the retention time (in minutes) and the area under the ultraviolet absorption peak at 254 nm., which is uniquely identifiable for compounds of this type.

The standards used for assignment of retention time and 254 nm. absorption were separately prepared linear compounds including bisphenol A mono- and diphenyl carbonate and the diphenyl carbonate of bisphenol A dimer. Higher oligomers were detected by analogy.

An important feature of the bischloroformate constituents of the compositions of this invention is the low percentage therein (no more than 10% by weight of the compounds of formula I) or higher oligomers; that is, oligomers in which n is greater than 3. The presence of such higher oligomers detracts substantially from the utility of bischloroformate compositions for the preparation of cyclic polycarbonate oligomers, a principal utility of the compositions of this invention. The chloroformate constituents typically include about 45–90% monomeric bischloroformates, and may also include dimers, trimers and, in some instances, monochloroformates.

Also present in the compositions of the invention may be materials not contributing materially to their novel and useful properties. These are most often substantially inert organic liquids which are solvents for the bischloroformates. Examples of such liquids are provided hereinafter.

Another aspect of the present invention is a method for preparing chloroformate compositions, and especially dihydroxy compound bischloroformate compositions comprising principally monomers, dimers and trimers (i.e., compounds of formula I wherein n is from 1 to 3). Said method comprises passing phosgene into a heterogeneous mixture of a substantially inert organic liquid and a hydroxy compound of the formula $$R^2(OH)_x, \qquad (III)$$

wherein $R^2$ is an aliphatic, alicyclic or aromatic radical and x is at least 1, said solution being maintained at a temperature within the range of about 10°–40° C., with the proviso that the phosgene addition rate is high enough to effect rapid and complete reaction of phosgene with dissolved hydroxy compound when x is greater than 1 and the temperature is above 30° C., and simultaneously introducing a hydrogen chloride scavenger comprising an aqueous alkali metal or alkaline earth metal base solution as necessary while maintaining a pH in the range of 0.5–8 in the aqueous phase; the ratio of equivalents of total phosgene used to hydroxy compound being about 1.0–1.1:1.

As will be apparent from a comparison of formulas I and III, the hydroxy compounds which are useful in the method of this invention include monohydroxy, dihydroxy, trihydroxy and other polyhydroxy compounds. The value of x is usually 1 or 2 and especially 2. The $R^2$ value is usually an aromatic radical but may also be aliphatic or alicyclic; when it is aliphatic or alicyclic, it is most often a hydrocarbon radical free from acetylenic and usually also from olefinic unsaturation. Illustrative $R^2$ values when x is 1 are 1-butyl, 2-butyl, 1-hexyl, cyclohexyl and phenyl. When x is 2, $R^2$ may be a radical of the type previously listed with respect to $R^1$; thus, the useful dihydroxy compounds include ethylene glycol, propylene glycol, trimethylene glycol, tetramethylene glycol, hexamethylene glycol, dodecamethylene glycol, poly-1,4-(2-butenylene)glycol, poly-1,10(2-ethyldecylene)glycol, 1,3-cyclopentanediol, 1,3-cyclohexanediol, 1,4-cyclohexanediol, resorcinol, hydroquinone, 4,4'-diphenol, bisphenol A and 1,4-bis(hydroxymethyl)benzene.

The preferred diols are those in which $R^2$ is aromatic and especially bisphenols having the formula $$HO-A^1-Y-A^2-OH,$$

wherein $A^1$, $A^2$ and Y are as previously defined. Because such bisphenols are particularly useful in the method of this invention, frequent reference will be made to them hereinafter. However, it should be understood that other mono- and polyhydroxy compounds can be substituted for the bisphenols. Bisphenol A is most preferred.

According to the method of this invention, the bisphenol is combined with a substantially inert organic liquid to form a heterogeneous mixture. Thus, the liquid need not dissolve substantial amounts of the bisphenol. It should be a solvent for the chloroformate product, and should generally be substantially insoluble in water. Illustrative liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

Phosgene is passed into the heterogeneous bisphenol-liquid mixture while said mixture is maintained at a temperature within the range of about 10°–40° C. The phosgene is ordinarily introduced in gaseous form, but its introduction as a liquid or as a solution in a suitable solvent is within the scope of the invention.

When temperatures above 30° C. are employed and x is greater than 1, the phosgene flow rate is maintained at a level high enough to effect rapid and complete reaction of phosgene with the portion of the hydroxy compound which is dissolved in the organic liquid. This is necessary because any hydroxy compound which does not react with phosgene may react with bischloroformate to yield higher bischloroformate oligomers, whose percentage in the bischloroformate composition should be minimized. In general, under these conditions the time for complete reaction of hydroxy compound should be 30 minutes or less. At lower temperatures, phosgene solubility increases and hydroxy compound solubility decreases to the point where phosgene competes successfully with bischloroformate irrespective of its addition rate.

The above-defined conditions are most reliably maintained when x is greater than 1 and at temperatures above 30° C. by maintaining a phosgene flow rate of at least 0.15 and preferably about 0.2-0.4 equivalent per equivalent of hydroxy compound per minute. (For the purposes of this invention, the equivalent weight of a hydroxy compound is its molecular weight divided by the number of hydroxy groups therein, and that of phosgene is equal to its molecular weight.) At lower temperatures or when x is 1 the phosgene flow rate is not critical, but a value within the range of about 0.05-0.2 equivalent per equivalent of hydroxy compound per minute is usually preferred at temperatures up to about 25° C., and a value of about 0.05-0.25 equivalent per equivalent of hydroxy compound per minute may be employed at 25°-30° C.

The acidity of the reaction mixture is another important aspect of the method of this invention. Contrary to most of the suggestions in the prior art, it has been discovered that relatively low acidity values are disadvantageous since they increase the amount of monomer bischloroformate in the product. On the other hand, hydrogen chloride is the strongly acidic by-product of the reaction between hydroxy compound and phosgene and/or bischloroformate, and its removal promotes said reaction. Therefore, a hydrogen chloride scavenger comprising an aqueous solution of alkali metal or alkaline earth metal base, most often a hydroxide such as sodium hydroxide, potassium hydroxide or calcium hydroxide, is added as necessary to maintain a pH no higher than 8, usually within the range of 0.5-8 and preferably 2-8, in the aqueous phase in contact with said heterogeneous mixture. (In the absence of base, the pH in any aqueous phase would approach zero as hydrogen chloride concentration increased.) The proportion of base required can readily be determined by routine experimentation; it is usually about 1.25-1.5 equivalents per equivalent of bisphenol. The concentration of the added base solution is not critical and may be, for example, about 1-16N.

A principal advantage of the method of this invention is the relatively low proportion of phosgene necessary to afford the desired chloroformate. It is necessary to employ only about 1.0-1.1 and preferably 1.05-1.1 equivalent of phosgene per equivalent of bisphenol.

Following preparation of the chloroformate composition by the method of this invention, solvent may be removed and individual components of the composition, such as bisphenol bischloroformate, may be separated by conventional means such as distillation, chromatography, fractional crystallization or the like. Such operations are frequently unnecessary, however, since for many purposes the chloroformate compositions of this invention may be used without solvent removal or purification.

The method of this invention is illustrated by the following examples.

EXAMPLES 1-7

A heterogeneous mixture of bisphenol A and methylene chloride was stirred at a constant temperature as phosgene was passed in at a constant flow rate, for a period of time to provide 1.05 equivalents of phosgene per equivalent of bisphenol A. Simultaneously with the phosgene addition, 5N aqueous sodium hydroxide solution was added to maintain the pH within the desired range. The mixture was stirred for an additional 15 minutes and the methylene chloride layer was removed, washed once with 0.1N aqueous hydrochloric acid, end-capped by the addition of an equimolar mixture of phenol and triethylamine, and chromatographically analyzed as previously described. The reaction conditions and product analyses are given in the following table. The "control" is not according to the present invention by reason of the high temperature and low phosgene flow rate, and is provided for comparison.

|  | Example | | | | | | | |
|---|---|---|---|---|---|---|---|---|
|  | 1 | 2 | 3 | 4 | 5 | 6 | 7 | Control |
| Bisphenol A (BPA): | | | | | | | | |
| Amount, meq. | 100 | 100 | 200 | 200 | 200 | 224 | 224 | 600 |
| Equivs. per liter of methylene chloride | 0.6 | 0.6 | 1.6 | 1.6 | 2.0 | 2.0 | 2.0 | 2.0 |
| Phosgene flow rate, eq./eq. BPA/min. | 0.174 | 0.174 | 0.101 | 0.101 | 0.051 | 0.179 | 0.359 | 0.033 |
| pH of aqueous phase | 4-5 | 7-8 | 3-4 | 5-8 | 0.5-2 | 2-5 | 2-5 | 3-4 |
| Temperature, °C. | 20 | 20 | 30 | 30 | 30 | 40* | 40* | 40* |
| Product, % by wt.: | | | | | | | | |
| BPA bischloroformate | 87 | 79 | 46 | 49 | 50 | 67 | 83 | 17 |
| Monochloroformates | 4.5 | 11.2 | 14 | 12 | 21 | 5 | 0 | 5 |
| Dimer bischloforormate | 8 | 9 | 21 | 21 | 19 | 18 | 11 | 20 |
| Trimer bischloforormate | 0 | 4 | 10 | 9 | 6 | 5 | 3 | 18 |
| Higher bischloforormates | 0 | 0 | 8 | 8 | 3 | 2 | 1 | 24 |

*Reflux temperature of methylene chloride.

A comparison of Examples 6 and 7 with the control clearly shows the effect on product distribution of the phosgene flow rate, since the low flow rate of the control produces 24% higher bischloroformates while 2% or less are obtained at higher flow rates. The combined effect of pH and flow rate is indicated by Examples 3-5, conducted at 30° and a relatively low phosgene flow rate which results in the formation of 8% higher bischloroformates at higher pH values (a relatively high figure when compared with those at higher flow rates irrespective of temperature), and only 3% higher bischloroformate (but 21% monochloroformates) at a maximum pH of 2.

EXAMPLES 8-13

The procedure of Example 7 was repeated, replacing bisphenol A on an equimolar basis with the following dihydroxy compounds:
Example 8—hydroquinone.
Example 9—2,2-bis(4-hydroxy-3,5-dimethylphenyl)-propane.

Example 10—2,2-bis(4-hydroxy-3,5-dibromophenyl)propane.
Example 11—1,1-bis(4-hydroxyphenyl)cyclohexane.
Example 12—1,1-bis(4-hydroxyphenyl)cyclododecane.
Example 13—1,1-bis(4-hydroxyphenyl)-2,2-dichloroethylene.

In each instance, similar bischloroformate compositions comprising a substantial proportion of monomer bischloroformate were obtained.

EXAMPLES 14-17

The procedure of Example 7 is repeated, replacing bisphenol A on an equimolar basis with the following dihydroxy compounds:
Example 14—resorcinol.
Example 15—bis(4-hydroxyphenyl)methane.
Example 16—2,2-bis(4-hydroxyphenyl)butane.
Example 17—bis(4-hydroxyphenyl)ether.

In each instance, similar bischloroformate compositions comprising a substantial proportion of monomer bischloroformate are obtained.

What is claimed is:

1. A method for preparing chloroformate compositions which comprises passing phosgene into a heterogeneous mixture of a substantially inert organic liquid and a hydroxy compound of the formula $$R^2(OH)_x, \tag{III}$$

wherein $R^2$ is an aliphatic or alicyclic radical free from acetylenic unsaturation or an aromatic radical and x is at least 1, said mixture being maintained at a temperature within the range of about 10°-40° C., with the proviso that the phosgene addition rate is high enough to effect rapid and complete reaction of phosgene with dissolved hydroxy compound when x is greater than 1 and the temperature is above 30° C., and simultaneously introducing a hydrogen chloride scavenger comprising an aqueous alkali metal or alkaline earth metal hydroxide solution as necessary while maintaining a pH in the range of 0.5-8 in the aqueous phase; the ratio of equivalents of total phosgene used to hydroxy compound being about 1.0-1.1:1.

2. A method according to claim 1 wherein the pH is maintained in the range of 2-8.

3. A method according to claim 2 wherein the hydrogen chloride scavenger is a sodium hydroxide solution.

4. A method according to claim 3 wherein x is 2 and $R^2$ is an aromatic radical.

5. A method according to claim 4 wherein $R^2$ has the formula $$-A^1-Y-A^2-, \tag{II}$$

wherein each of $A^1$ and $A^2$ is a single-ring divalent aromatic radical and Y is a bridging radical in which one or two atoms separate $A^1$ from $A^2$.

6. A method according to claim 5 wherein each of $A^1$ and $A^2$ is p-phenylene.

7. A method according to claim 6 wherein Y is isopropylidene.

8. A method according to claim 7 wherein the temperature is up to about 25° C. and the phosgene flow rate is about 0.05-0.2 equivalent per equivalent of hydroxy compound per minute.

9. A method according to claim 7 wherein the temperature is 25°-30° C. and the phosgene flow rate is about 0.05-0.25 equivalent per equivalent of hydroxy compound per minute.

10. A method according to claim 7 wherein the temperature is above 30° C. and the phosgene flow rate is about 0.2-0.4 equivalent per equivalent of hydroxy compound per minute.

* * * * *

UNITED STATES PATENT AND TRADEMARK OFFICE
CERTIFICATE OF CORRECTION

PATENT NO. : 4,638,077

DATED : January 20, 1987

INVENTOR(S) : Daniel J. Brunelle and Thomas G. Shannon

It is certified that error appears in the above-identified patent and that said Letters Patent is hereby corrected as shown below:

Title page, column 1, item 75, cancel the name of Niles R. Rosenquist, Evansville, Ind., as a joint inventor.

Signed and Sealed this

Seventh Day of April, 1987

Attest:

DONALD J. QUIGG

Attesting Officer

Commissioner of Patents and Trademarks